United States Patent
Eckersall et al.

(10) Patent No.: US 7,172,872 B1
(45) Date of Patent: Feb. 6, 2007

(54) ASSAYS FOR MASTITIS DETECTING HAPTOGLOBIN IN MILK

(75) Inventors: Peter David Eckersall, Glasgow (GB); Julie Lydia Fitzpatrick, Glasgow (GB); Andrea Mary Nolan, Glasgow (GB); Christopher McComb, Glasgow (GB)

(73) Assignee: The University Court of the University of Glasgow, Glasgow (GB)

( * ) Notice: Subject to any disclaimer, the term of this patent is extended or adjusted under 35 U.S.C. 154(b) by 714 days.

(21) Appl. No.: 10/110,556

(22) PCT Filed: Oct. 12, 2000

(86) PCT No.: PCT/GB00/03925

§ 371 (c)(1),
(2), (4) Date: Jul. 23, 2002

(87) PCT Pub. No.: WO01/27631

PCT Pub. Date: Apr. 19, 2001

(30) Foreign Application Priority Data

Oct. 12, 1999 (GB) .................................. 9924180.4

(51) Int. Cl.
*G01N 33/53* (2006.01)
*G01N 33/543* (2006.01)

(52) U.S. Cl. ..................... 435/7.1; 435/7.21; 435/7.92; 435/283.1; 435/325; 436/514; 436/518; 436/540; 424/130.1

(58) Field of Classification Search ................. 435/7.1, 435/7.21, 7.92, 325, 283.1; 436/514, 518, 436/540; 424/130.1
See application file for complete search history.

(56) References Cited

U.S. PATENT DOCUMENTS 5,552,295 A 9/1996 Stanker et al. ............. 435/7.92

FOREIGN PATENT DOCUMENTS

WO   WO 95/22767   8/1995
WO   WO 99/21003   4/1999
WO   WO99/24833   5/1999

OTHER PUBLICATIONS

Sheffield et al. (Veterinary Immunology and Immunopathology, 42, 1994, pp. 171-183).*
Wadsworth and Hanson (Experientia, 1959, vol. 15, pp. 473-474).*
Skinner et al. (The Veterinary Record, Feb. 16, 1991, pp. 147-149,128 (7)).*
Morimatsu et al. (Veterinary Immunology and Immunopathology, 1992, pp. 365-372, 33 (4)).*
Barth et al. (English Abstract Only, Milchwissenchaft, 1999, vol. 54, No. 2, pp. 66-69.*
Riollet et al., "Kinetics of Cells and Cytokines During Immune-Mediated Inflammatory in the Mammary Gland of Cows Systemically Immunized with *Staphylococcus aureus* α-toxin," *Inflamm. Res.* 49: 486-496 (2000).
Young et al., "Serum Haptoglobin to Monitor the Acute Phase Response in Bovine Mastitis," *Immunology*, 95:1 132 (Dec. 1998).
Erskine, R. J. et al. "Herd management and prevalence of mastitis in dairy herds with high and low somatic cell counts" *Journal of the American Veterinary Medical Association* 190(11) pp. 1411-1416. (1987).
Esslemont, R.J. and I. Spincer. "DAISY The Information System" Report No. 2: The Incidence and Costs of Disease in Dairy Herds *University of Reading* (1993).
Hamann, J. et al. "C-reactive protein in milk of healthy and subclinically disease bovine udder quarters". *Udder Health.* 52 pp. 546-550. (1997).
Menzies, F.D., et al. "A study of mortality among suckler and dairy cows in Northern Ireland in 1992" *The Veterinary Record* 137 pp. 531-536 (1995).
Pyörälä, S and E. Pyörälä. "Accuracy of methods using somatic cellcount and N-Acetyl-β-D-Glucosaminidase activity in milk to assess the bacteriological cure of bovine clinical mastitis" *The Journal of Dairy Science.* 80 pp. 2820-2825 (1997).

* cited by examiner

Primary Examiner—Long V. Le
Assistant Examiner—Lisa V Cook
(74) *Attorney, Agent, or Firm*—Myers Bigel Sibley & Sajovec, PA

(57) ABSTRACT

An assay for the detection of haptoglobin (Hp) in milk using an Hp-specific antibody as a means to predict or detect mastitis or subclinical mastitis by way of Hp being an associated marker and/or to test the quality of milk, in, for example, dairy cattle.

13 Claims, 1 Drawing Sheet

ASSAYS FOR MASTITIS DETECTING HAPTOGLOBIN IN MILK

RELATED APPLICATIONS

This application claims priority under 35 U.S.C. § 371 from PCT Application No. PCT/GB00/03925, filed in English on Oct. 12, 2000, which claims the benefit of Great Britain Application Serial No. 9924180.4 filed on Oct. 12, 1999, the disclosures of which are incorporated by reference herein in their entireties.

BACKGROUND OF THE INVENTION

The present invention relates to an assay for the detection of haptoglobin (Hp) in milk as a means to predict or detect mastitis or subclinical mastitis in for example dairy cattle.

Mastitis is very costly to the dairy industry due to discarded milk, reduced yield, milk of lower value, increased rates of premature culling and occasional mortality (Esslemont and Spincer, 1993) and is recognised as one of the major diseases adversely affecting dairy cow welfare (Menzies, 1995). Strategies for early detection of mastitis are particularly beneficial to the dairy industry in terms of early treatment of cattle thus improving milk production whilst generally maintaining milk quality and health status of the animals.

Detection of mastitis pathogens typically forms a basis of mastitis diagnosis (Hamann et al, 1997). For example, the bacteria *Staphyloccus aureus* is known to be a cause of clinical and subclinical mastitis in dairy cattle (Erskine et al, 1987).

GB98/03132 for example describes an immunological assay using a *Staphylococcus aureus* antigen mixed with a sample of blood taken from dairy cattle to induce a proliferative response in the blood cells.

Additionally measurement of a level of cell proliferation as a means of detecting mastitis may be determined by a number of methods including addition of radioactive nucleotides followed by scintillation counting. However, such tests involve taking a blood sample, which may not be desirable.

Further to this, somatic cell counting (SCC) is often used as a means to detect mastitis where a high somatic cell count is indicative of this condition (Pyörälä and Pyörälä, 1997). However, this method proves to have an undesirable amount of false positive results giving an inaccurate measurement.

Other tests used to detect mastitis include those involved in detecting inflammatory changes. For example, a group of proteins, known as acute phase proteins show a dramatic increase in concentration in blood in response to infection, inflammation or trauma. Such proteins include Haptoglobin (Hp), carbon-reactive protein (CRP) and serum amyloid A (SAA).

WO9522767 discloses an assay for determining CRP in mammals, where the sample is milk. However a later study by Hamann et al, 1997, raised doubt as to whether or not the determination of CRP levels could be used to predict infection, such as mastitis.

Presently, assays for the detection of another acute phase protein, namely haptoglobin, in blood, serum or plasma samples are based on an immunoassay; the ability of Hp to bind to haemoglobin (Hb); or the determination of the peroxidase activity of an haptoglobin/haemoglobin complex.

Hp in human plasma is typically measured by antibody based methods with antiserum specific for human Hp. However, such tests again require blood sampling and more often than not, some form of fractioning of the blood to obtain a plasma sample. This it will be appreciated can be time consuming and requires blood sampling to be carried out.

Original assays based on Hp-Hb binding depended on the finding that formation of the Hp-Hb complex alters the spectrophotomeric absorption characteristic of Hb in proportion to the concentration of Hp in a plasma sample. GB98/03407 discloses an additional method for determining Hp in blood by measuring, using chemical means, the peroxidase activity of an haptoglobin/haemoglobin complex. However, this assay may not be applicable in the measurement of Hp in milk since there is a non-Hp associated peroxidase activity in milk which is likely to affect such an assay.

SUMMARY OF THE INVENTION

It is an object of the present invention to obviate and/or mitigate some of the above disadvantages.

The present invention is based in part on the discovery by the present inventor(s) that haptoglobin in milk may be detected with a high specificity.

The present invention therefore provides an immunoassay for detecting in vitro the presence of haptoglobin in a sample of milk, comprising the steps of:

a) obtaining the sample of milk;

b) bringing the sample of milk into contact with a reagent comprising an antibody specific for haptoglobin in order that haptoglobin present in the sample of milk may form an haptoglobin/antibody complex; and c) detecting the haptoglobin/antibody complex.

DETAILED DESCRIPTION OF THE INVENTION

Figure 1:
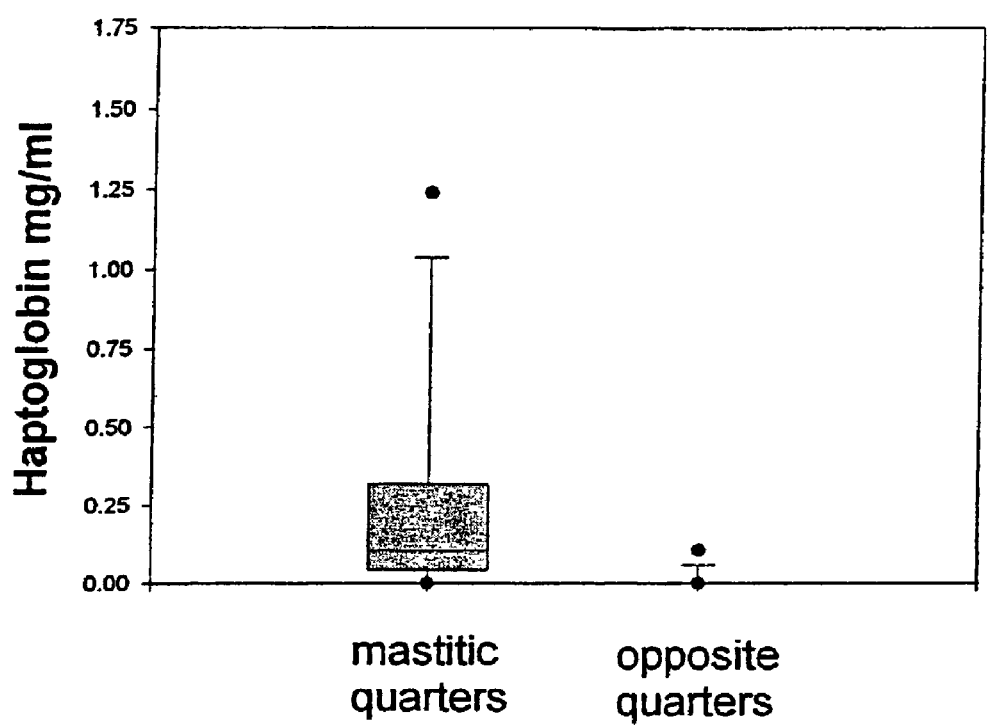
FIG. 1 shows the concentration of haptoglobin in milk from infected quarters and diagonally opposite control quarters.

The assay is generally used to predict or detect mastitis or sub-clinical mastitis by way of haptoglobin being an associated marker. However, the assay may be used to test the quality of milk.

The immunoassay may take any of a variety of known forms wherein antigen and antibody react to form a complex and the resulting complex is detected. Such forms include immunoassays based on nephelometry, diffusion assays, agglutination assays, ELISA based assays, radioimmunoassay, immunochromatography, electrometric immunoassay, surface effect immunoassay and the like. The assay system incorporating the antibody specific for haptoglobin may therefore be in the form of a gel, solution, paper, membrane, biosensor or the like, in order that any haptoglobin present in the sample of milk can come into contact with the antibody. Ideally, such forms would be used to detect haptoglobin in milk by use of an automated system during milking.

In one embodiment the immunoassay of the present invention may be in the form of single radial immunodiffusion (SRID) assay. In such an assay milk is placed in a well cut into a layer of agar (or agarose) gel and is allowed to diffuse into the surrounding agar which contains suitably diluted antiserum comprising an haptoglobin-specific antibody. The higher the concentration of antigen the further the diffusion distance.

The SRID assay can be used to detect and determine the concentration of haptoglobin antigen in milk from the size of precipitation ring formed by the haptoglobin present in the milk complexing and precipitating with the antibody. The ring of precipitation may be detected by suitable means, such as by protein staining techniques known in the art and may be correlated with a standard calibration curve obtained using standards of known haptoglobin antigen concentration.

In the other forms of assay mentioned above, the haptoglobin/antibody complex may be detected using conventional techniques. For example the antibody may be labelled directly or indirectly with a radioisotope, a fluorescent marker, or an enzyme capable of giving a coloured reaction product on addition of a suitable substrate. Indirect labelling may involve the addition of a labelled antibody which is specifically reactive with the antibody of the haptoglobin/antibody complex.

Typically the sample may be any milk sample. Generally speaking the sample may be obtained from any milk-producing animal, such as, mammalian animals, including humans. However the milk sample is generally taken from commercial milk producing animals such as cows, sheep and goats, where the early detection of mastitis is important in order to improve milk production.

If appropriate the milk sample may be diluted prior to subjecting it to the assay.

Typically, the antibody may be provided by way of a sample of serum containing a high titer of antibody specific to haptoglobin. Alternatively, a monoclonal antibody specific to haptoglobin may be used. Techniques for obtaining antibodies, such as polyclonal or monoclonal antibodies are well known in the art.

The present invention will now be further described by way of non-limiting example.

EXAMPLE 1

Immunoassay for Haptoglobin in Milk to Detect Mastitis

Reagents

Stock Solutions

Tris buffered saline (TBS) at 500 mmol/l tris pH7.4 and 9.0% NaCl.

Destain solution: a 9:9:2 mixture of ethanol:dH$_2$O:acetic acid.

Coomassie brilliant blue stain (G250), 0.5% in destain solution.

Working Solutions

TBS stock solution diluted 10 times in distilled water (dH$_2$O).

A standard curve of a series of dilutions in 0.9% NaCl of a serum sample of known haptoglobin concentration to give standard concentrations over the range 1.4–0.02 mg/ml.

Other Material

Agarose and Gelbond sheets for attachment of agarose gel (Sigma Chem Co, Poole, UK).

Samples

Milk samples were collected by hand-stripping from the quarter of 29 dairy cows with clinical mastitis at the commercial herd of the University of Glasgow. Mastitis was diagnosed by presence of clots in the milk (defined as mild mastitis) or by the presence of clots plus observable inflammation in the infected quarter (defined as moderate mastitis). Samples were also submitted for somatic cell counting and routine bacteriology. A milk sample was also taken from the quarter diagonally opposite the infected quarter to act as a intra-animal control. Samples were also taken from two diagonally opposite quarters of 16 healthy cows from the same herd of dairy cows to act as between animal controls.

Method

Agarose (0.225 g to give a final concentration of 1.5%) was added to 15 ml of TBS buffer and dissolved by heating for 60 s in a microwave. The molten agarose was placed in a water bath at 56° C. and allowed to equilibrate. An appropriate volume of ovine antiserum to bovine haptoglobin (0.6 ml) was added and gently mixed with the agarose. The agarose containing antibody was poured onto a horizontal sheet of GELBOND® (75 mm×100 mm) (Camden Corporation), a transparent, flexible polyester film, on a level surface and allowed to solidify. Holes were punched in the agarose (2.0 mm diameter) and excess agarose removed. Sample (diluted if necessary in 0.9% NaCl) or standards were pipetted into the wells (8 µl) and the agarose gel was incubated in a humidity chamber for up to 48 hrs at 4° C.

The agarose gel was inspected visually and then washed in saline (0.9% NaCl) for 30 min, covered with filter paper and several layers of absorbent paper and pressed with a weight for 30 minutes to squeeze buffer and non precipitated protein from the gel. The gel was washed for 30 min in saline and pressed for a further two cycles with a final wash in distilled water and a final press. The gel plate was dried in a 37° C. incubator, then placed in the Coomassie blue stain for 10–15 minutes and transferred to destain solution until the background was clear. The diameter of the circles of precipitation which were stained dark blue was measured and those from the standards plotted against concentration on 3 cycle log paper. The test results were read off the standard curve.

Results a) Haptoglobin in Milk from Infected Quarters and Diagonally Opposite Control Quarters.

The concentration of haptoglobin in milk from infected quarters ranged from <0.02 mg/ml (undetectable) to 2.15 mg/ml (Table 1, FIG. 1). Four of the samples had undetectable levels of haptoglobin. In contrast, 25 out of 29 of the milk samples from the quarters opposite those with mastitis had undetectable levels of haptoglobin.

TABLE 1

Haptoglobin in milk from cows with clinical mastitis Hp mg/ml

| Animal | Infected quarter | Opposite quarter |
|---|---|---|
| 1 | 2.15 | 0 |
| 2 | 0 | 0 |
| 3 | 0.325 | 0 |
| 4 | 0.115 | 0 |
| 5 | 0.05 | 0 |
| 6 | 0.94 | 0 |
| 7 | 0.02 | 0 |
| 8 | 0.02 | 0 |
| 9 | 0.066 | 0 |
| 10 | 0.12 | 0 |
| 11 | 0.09 | 0.56 |
| 12 | 0 | 0 |

TABLE 1-continued

Haptoglobin in milk from cows with clinical mastitis
Hp mg/ml

| Animal | Infected quarter | Opposite quarter |
|---|---|---|
| 13 | 1.1 | 0 |
| 14 | 0 | 0.028 |
| 15 | 0.098 | 0 |
| 16 | 1.19 | 0 |
| 17 | 0.315 | 0 |
| 18 | 0.315 | 0 |
| 19 | 0.082 | 0.082 |
| 20 | 0.076 | 0 |
| 21 | 0.305 | 0 |
| 22 | 0.68 | 0 |
| 23 | 0.105 | 0 |
| 24 | 0.05 | 0 |
| 25 | 0 | 0 |
| 26 | 0.02 | 0.8 |
| 27 | 0.8 | 0 |
| 28 | 0.21 | 0 |
| 29 | 0.125 | 0 | b) Haptoglobin in Milk from Diagonally Opposite Quarters in Healthy Control Animals.

None of the milk samples from quarters of healthy cows (Table 2) had detectable concentrations of haptoglobin.

TABLE 2

Haptoglobin in milk from quarters of healthy cows

| Animal | Quarter a | Quarter b |
|---|---|---|
| 30 | 0 | 0 |
| 31 | 0 | 0 |
| 32 | 0 | 0 |
| 33 | 0 | 0 |
| 34 | 0 | 0 |
| 35 | 0 | 0 |
| 36 | 0 | 0 |
| 37 | 0 | 0 |
| 38 | 0 | 0 |
| 39 | 0 | 0 |
| 40 | 0 | 0 |
| 41 | 0 | 0 |
| 42 | 0 | 0 |
| 43 | 0 | 0 |
| 44 | 0 | 0 |
| 45 | 0 | 0 | c) Assessment of Measuring Haptoglobin in Milk for the Detection of Mastitis.

TABLE 3

Diagnostic value of haptoglobin in milk for the detection of mastitis

|  | Diseased v healthy animals | Infected quarters v all apparently healthy quarters* |
|---|---|---|
| Sensitivity % | 86 | 86 |
| Specificity % | 100 | 93 |
| Predictive value of positive test % | 100 | 86 |
| Predictive value of negative test % | 80 | 93 |
| Efficiency % | 91 | 93 |

*combination of quarters from healthy cows and quarters diagonally opposite those with mastitis These results (Table 3) show that a test for milk haptoglobin has a specificity of 100% for diagnosis of an animal with mastitis indicating that no false positive results were obtained. This is a major advantage over currently used tests such as somatic cell counting. This discovery relates to the acute phase response of haptoglobin, as undetectable levels of this protein are present in the circulation of normal animals, only appearing in the blood during an acute phase response as a direct result of infection or inflammation. Without wishing to be bound by theory it is thought that haptoglobin in milk is derived from serum haptoglobin and therefore in healthy dairy cows the haptoglobin concentration in milk will always be lower than the assay limits of detection. It is further presumed that haptoglobin appears in milk after mastitis causes the stimulation of cytokine production by immune cells in the udder. These mediators lead to increased release from the liver of haptoglobin which is able to pass from the blood into the infected quarter due to a breakdown of the blood-mammary barrier which is another consequence of the inflammatory reaction to the mastitis in that quarter.

In comparison of infected quarters to all apparently healthy quarters the results show that a test for milk haptoglobin has a specificity of 93%. This was due to 4 of the milk samples from quarters opposite infected quarters having detectable levels of haptoglobin. It is possible that some or all of these apparently healthy quarters had sub-clinical mastitis but this needs to be confirmed by further study. Even if these quarters did not have subclinical mastitis, it would still be apparent that leakage of serum protein had occurred which affects the milk quality and it is therefore apparent to the skilled operator that the haptoglobin test detects deterioration in milk quality as well as mastitis.

The sensitivity of the milk haptoglobin as a marker for mastitis was 86% in both comparison of individual animals and between quarters as 4 false negative results were recorded in milk from infected quarters.

The major advance in mastitis diagnosis from measuring milk haptoglobin is the high specificity and the predictive value of a positive test derived from these findings. Therefore any animal with a positive test for haptoglobin in milk is identified as having mastitis, thus allowing early interventions including therapy.

REFERENCES

1. Esslemont and Spincer, (1993). The Dairy Report No. 2, Department of Agriculture, University of Reading.
2. Menzies et al, (1995). Vet. Rec., 137, 531–536.
3. Hamman, J., et al, (1997). Milchwissenschaft, 52, 546–550.
4. Erskine et al, (1987). JAVMA, 190, 1411–1416.
5. Pyörälä, S. And Pyörälä, E., (1997). J. Dairy Sci., 80, 2820–2825.

The invention claimed is:

1. An immunoassay method for detecting in vitro the presence of haptoglobin in a sample of milk, comprising the steps of:
   obtaining the sample of milk, wherein the sample is a sample of cow, sheep or goat milk;
   bringing any haptoglobin present in the sample of milk into contact with a reagent comprising an antibody specific for haptoglobin in order that haptoglobin present in the sample of milk may form an haptoglobin/antibody complex; and
   detecting the haptoglobin/antibody complex.

2. An immunoassay method according to claim 1 wherein detection of the haptoglobin/antibody complex predicts or detects mastitis or sub-clinical mastitis.

3. An immunoassay method according to claim 1 wherein said immunoassay includes, nephelometry, diffusion assays, agglutination assays, ELISA based assays, radioimmunoassay, immunochromatography, electrometric immunoassay, or surface effect immunoassay.

4. An immunoassay method according to claim 3 wherein said immunoassay is a single radial immunodiffusion (SRID) assay.

5. An immunoassay method according to claim 1 wherein said antibody specific for haptoglobin is incorporated into assay substrates, including a gel, solution, paper, membrane, or biosensor.

6. An immunoassay method according to claim 5 wherein said gel is in the form of agar or agarose gel.

7. An immunoassay method according to claim 1 wherein said haptoglobin/antibody complex is formed by allowing a sample to diffuse into agar which contains suitably diluted antiserum comprising a haptoglobin-specific antibody.

8. An immunoassay method according to claim 1 wherein said antibody is labelled directly or indirectly with a radio-isotope, a fluorescent marker or an enzyme capable of giving a coloured reaction product on addition of a suitable substrate.

9. An immunoassay method according to claim 8 wherein said indirect labelling involves the addition of a labelled antibody which is specifically reactive with the antibody of the haptoglobin/antibody complex.

10. An immunoassay method according to claim 1 wherein said sample is diluted prior to subjecting it to the assay.

11. An immunoassay method according to claim 1 wherein said immunoassay detects haptoglobin in milk with an automated system during milking.

12. An immunoassay method according to claim 1 wherein the antibody is provided in a sample of serum containing an antibody specific to haptoglobin.

13. An immunoassay method according to claim 1 wherein the antibody is a monoclonal antibody specific to haptoglobin.

* * * * *